(12) United States Patent
Leuthold et al.

(10) Patent No.: US 11,612,861 B2
(45) Date of Patent: Mar. 28, 2023

(54) CROSSFLOW FILTRATION UNIT FOR CONTINUOUS DIAFILTRATION

(71) Applicant: Sartorius Stedim Biotech GmbH, Goettingen (DE)

(72) Inventors: Martin Leuthold, Goettingen (DE); Ulrich Grummert, Bad Sooden-Allendorf (DE); Peter Schmidt, Bovenden (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 103 days.

(21) Appl. No.: 16/150,685

(22) Filed: Oct. 3, 2018

(65) Prior Publication Data

US 2019/0030486 A1   Jan. 31, 2019

Related U.S. Application Data

(63) Continuation of application No. PCT/EP2017/000427, filed on Apr. 5, 2017.

(30) Foreign Application Priority Data

Apr. 5, 2016 (DE) ...................... 10 2016 004 115.3

(51) Int. Cl.
*B01D 61/14* (2006.01)
*A23C 9/142* (2006.01)
(Continued)

(52) U.S. Cl.
CPC ............ *B01D 61/146* (2022.08); *A23C 9/142* (2013.01); *A61M 1/3417* (2014.02); *B01D 61/16* (2013.01);
(Continued)

(58) Field of Classification Search
None
See application file for complete search history.

(56) References Cited

U.S. PATENT DOCUMENTS

| 4,855,058 A | 8/1989 | Holland et al. |
| 5,730,712 A * | 3/1998 | Falkvall .................. A61M 1/16 |
| | | 210/321.8 |

(Continued)

FOREIGN PATENT DOCUMENTS

| DE | 3441249 C2 | 5/1985 |
| DE | 10022259 A1 | 11/2001 |
| EP | 0014166 A1 | 8/1980 |

OTHER PUBLICATIONS

EP International Search Report, PCT/EP2017/000427, dated Jun. 22, 2017, 2 pages.

(Continued)

*Primary Examiner* — Jonathan M Peo
(74) *Attorney, Agent, or Firm* — Edell, Shapiro & Finnan, LLC

(57) ABSTRACT

A crossflow filtration unit for continuous diafiltration of a feed fluid for obtaining a retentate and a permeate, a corresponding method for diafiltration and the use of the crossflow filtration unit are provided. The crossflow filtration unit includes a diafiltration channel, a flat first filter material, a retentate channel, a flat second filter material, and a permeate collection channel, arranged such that the flat first filter material delimits the diafiltration channel and the retentate channel from one another, and the flat second filter material delimits the retentate channel and the permeate collection channel from one another. The diafiltration channel is fluidly connected to at least one inlet for the diafiltration medium, the retentate channel is fluidly connected to at least one inlet for the feed fluid and to at least one outlet (Continued)

for the retentate. The permeate collection channel is fluidly connected to at least one outlet for the permeate.

21 Claims, 5 Drawing Sheets

(51) Int. Cl.
  *B01D 61/16* (2006.01)
  *B01D 63/08* (2006.01)
  *A61M 1/34* (2006.01)

(52) U.S. Cl.
  CPC ... *B01D 63/084* (2013.01); *A61M 2205/3331* (2013.01); *B01D 2311/04* (2013.01); *B01D 2311/25* (2013.01); *B01D 2313/143* (2013.01); *B01D 2315/06* (2013.01); *B01D 2315/10* (2013.01); *B01D 2317/022* (2013.01); *B01D 2319/06* (2013.01)

(56) References Cited

U.S. PATENT DOCUMENTS

| | | |
|---|---|---|
| 6,916,420 B2 | 7/2005 | Schmidt et al. |
| 2005/0258100 A1 | 11/2005 | Lightfoot |
| 2008/0237110 A1 | 10/2008 | Lightfoot et al. |
| 2016/0045655 A1* | 2/2016 | Charest ................. A61M 1/341 210/646 |

OTHER PUBLICATIONS

Xiaobing Zhang, "Treatment and Nursing of Clinical Common Diseases", Mar. 31, 2016, Yunnan Science and Technology Press, 3 pages.

* cited by examiner

CROSSFLOW FILTRATION UNIT FOR CONTINUOUS DIAFILTRATION

CROSS REFERENCE TO RELATED APPLICATIONS

This is a Continuation of International Application PCT/EP2017/000427, which has an international filing date of Apr. 5, 2017, and which was published by the World Intellectual Property Organization (WIPO) as WO2017/174192A1 on Oct. 12, 2017, the disclosure of which is incorporated in its entirety into the present Continuation by reference. The following disclosure is also based on and claims the benefit of and priority under 35 U.S.C. § 119(a) to German Patent Application No. DE 10 2016 004 115.3, filed Apr. 5, 2016, which is also incorporated in its entirety into the present Continuation by reference.

FIELD OF THE INVENTION

Aspects of the present invention relate to a crossflow filtration unit for continuous diafiltration of a feed fluid for obtaining a retentate and a permeate, a corresponding method for diafiltration and the use of the crossflow filtration unit.

BACKGROUND

In crossflow filtration, which can also be referred to as crossflow filtration or tangential flow filtration, a feed fluid ("feed") to be filtered flows tangentially over the surface of a filter material, which is usually a membrane, and, in so doing, is split into a retentate (concentrate) and a permeate (filtrate) of varying compositions.

The retentate flows over the surface of the filter material and can be removed after just a single pass ("single pass" mode), but the retentate can also be resupplied to the cycle, so that it repeatedly flows over the membrane surface. The permeate flows through the membrane perpendicular to the surface and is then discharged. Target substances to be recovered may be contained in the permeate (permeate substances) and/or in the retentate (retentate substances).

Crossflow filtration units are often used in the form of filter cassettes, as described, for example, in DE-PS 34 41 249. Filter cassettes comprise a plurality of adjacent crossflow filtration units (filter cells), which usually consist of repeated arrays of a retentate channel for the feed fluid or the retentate to be filtered, a flat membrane layer and a permeate collection channel. The permeate collection channel of the above filter cell is delimited from the retentate channel of the next filter cell by an additional flat membrane layer. Each retentate channel is connected to an inlet for the feed fluid to be filtered and to an outlet for the retentate in a fluid conducting (communicating) manner; and each permeate collection channel is connected to an outlet for the permeate in a fluid conducting manner.

With conventional filtration a feed fluid is separated into a retentate and a permeate. In diafiltration this separation is combined with a step of adding a diafiltration medium to the feed fluid/the retentate. This step makes it possible, for example, to free a common solution of target substance(s) and one or more additional substances from the other substances. For example, by diafiltration of a protein solution it is possible to achieve a buffer exchange or a desalting, optionally combined with a concentration.

A distinction is made between two basic types of diafiltration: the variable volume diafiltration (sometimes referred to as "discontinuous" diafiltration in the art) and the constant volume diafiltration (sometimes referred to as "continuous" diafiltration in the art).

SUMMARY

In variable volume diafiltration the filtration steps and the steps of adding a diafiltration medium alternate. Consequently in the course of this alternative method the volume of the retentate fluctuates, from which the term "discontinuous diafiltration" is derived. In constant volume diafiltration the volume of the retentate is kept constant in that both the filtration and the addition of the diafiltration medium take place continuously. However, the addition of the feed fluid is discontinuous and usually takes place only at the beginning of the process. Therefore, both variable volume diafiltration and constant volume diafiltration are discontinuous processes. In a discontinuous diafiltration process a specified volume of feed fluid has to be subjected completely to a process run before a new process run can be started ("batch" method). For reasons relating to cost effectiveness and efficiency, continuous processes, in which streams of substances can be continuously supplied and discharged, are preferable to discontinuous processes. Therefore, there is a need for a continuous diafiltration process.

Therefore, an object of the present invention is to provide a crossflow filtration unit that is suitable for continuous diafiltration.

The present invention relates to a crossflow filtration unit for continuous diafiltration of a feed fluid for obtaining a retentate and a permeate, said crossflow filtration unit at least comprising a diafiltration channel, a flat first filter material, a retentate channel, a flat second filter material and a permeate collection channel, arranged in such a way that the flat first filter material delimits the diafiltration channel and the retentate channel from one another, and the flat second filter material delimits the retentate channel and the permeate collection channel from one another, wherein the diafiltration channel is connected in a fluid conducting manner to at least one inlet for the diafiltration medium; the retentate channel is connected in a fluid conducting manner to at least one inlet for the feed fluid and to at least one outlet for the retentate; and the permeate collection channel is connected in a fluid conducting manner to at least one outlet for the permeate, and wherein the pore size or the molecular weight cut-off of the flat first filter material is at least as large as the pore size or the molecular weight cut-off of the flat second filter material. The pore size or the molecular weight cut-off of the flat first filter material is preferably larger than the pore size or the molecular weight cut-off of the flat second filter material.

The flat first filter material has preferably a molecular weight cut-off (MWCO) in the range of 30 kDa to 1,500 kDa. The flat second filter material has preferably a molecular weight cutoff in the range of 5 kDa to 1,500 kDa. The determination of the molecular weight cut-off can be carried out in accordance with the US standard ASTM E1343-90 ("Standard test method for molecular weight cutoff evaluation of flat sheet ultrafiltration membranes").

The flat first filter material has preferably a pore size of 0.01 to 50 µm, preferably 0.01 to 0.5 µm. The flat second filter material has preferably a pore size of less than 0.01 µm. The determination of the pore size, which is also referred to as the "largest pore diameter" or "dp" and in English as the "maximum pore size", can be carried out in accordance with the US standard ASTM F316-03 TEST METHOD A ("Standard test methods for pore size characteristics of membrane filters by bubble point and mean flow pore test").

Basic methods for characterizing membranes are described in the dissertation by Melanie Sossna "Structure Formation of Cellulose Ester Membranes", University of Hanover 2006, section 2.5 on pages 10 f., in particular, in Table 2-4.

According to the prior art (discontinuous diafiltration), the diafiltration medium is introduced between the crossflow filtration units, which are connected in series; or the feed fluid is diluted with the diafiltration medium, combined with preceding or subsequent concentration by crossflow filtration. However, the crossflow filtration unit of the present invention makes it possible to introduce a certain amount of the diafiltration medium into the retentate channel using suitable pressurization for optimal diafiltration. For example, the volume of the diafiltration medium can be, according to the invention, 0.1 to 15 times the volume of the feed fluid. The diafiltration medium is introduced preferably into the retentate channel in such a way that the entire available surface area of the flat first filter material is covered with the diafiltration medium. The crossflow filtration unit of the present invention makes it possible to obtain a diafiltration result that is improved in comparison to discontinuous diafiltration. In addition, the invention leads to a reduction in both the amount of time required for the process and the amount of equipment required.

In continuous diafiltration both the feed fluid and the diafiltration medium are added continuously so that the process does not have to be interrupted. As a result, the crossflow filtration unit of the invention makes it possible to run the process in an efficient and economical manner.

With the improved crossflow filtration unit of the invention, fluids such as liquids, emulsions, suspensions, beverages, like beer, wine, juice, water, milk and whey, beer wort, industrial and waste water, solutions in the pharmaceutical, medical, cosmetic, chemical, biotechnology, genetic engineering, environmental protection and laboratory sector, can be used as a feed fluid and can be diafiltered. The improved crossflow units can be used for the recovery of valuable materials; separation of substances, for example, macromolecules and biomolecules; for depyrogenation and sterilization of solutions; for the separation of pollutants from the fluids; for the (dia)filtration and concentration of biological solutions; for the separation of microorganisms, such as bacteria, yeasts, viruses and cell constituents, for the desalting of protein solutions and other biological media.

The crossflow filtration unit of the invention can be used particularly advantageously for filtration, diafiltration, concentration (reduction of the solvent or water content), and/or modification of the ion composition (for example, desalting or buffer exchange) of a solution, preferably a protein solution.

For the fluid present in the retentate channel, the terms feed fluid and retentate can be used synonymously.

The term "flat" indicates that the respective filter material lies substantially in a single plane. Preferably all filter materials lie more or less in planes that are substantially parallel to each other.

According to a preferred embodiment of the invention, the flat first filter material is a first filtration membrane. The flat second filter material is preferably a second filtration membrane. It is particularly preferred that the flat first filter material be a first filtration membrane and that the flat second filter material be a second filtration membrane.

In particular, a porous membrane in the ultrafiltration and microfiltration range is suitable as the first filter material. An ultrafiltration membrane can be used advantageously as the second filter material. This configuration allows a specified amount of diafiltration medium to be introduced into the retentate channel using suitable pressurization for optimal diafiltration. When pressure is applied, the entire available area of the flat first filter material is covered with the diafiltration medium.

The ultrafiltration membranes are characterized by pore sizes of less than 0.01 µm or by molecular weight cut-offs that are approximately in the molecular weight range of 5 to 1,500 kDa, while the microfiltration membranes exhibit pore sizes in the range of 0.01 to 50 µm, preferably 0.01 to 0.5 µm, or molecular weight cut-offs of 30 to 1,500 kDa. The filtration membranes may consist, for example, of polyvinylidene fluoride, cellulose and derivatives thereof, polyethersulfone or polysulfone, with crosslinked cellulose hydrate being particularly preferred.

The inlet for the feed fluid is mounted preferably in a first edge region of the crossflow filtration unit; and the outlet for the retentate is mounted in a second edge region of the crossflow filtration unit that faces the first edge region. Owing to this arrangement it is possible to define a substantially uniform direction of flow of the retentate from the inlet for the feed fluid, as the starting point, to the outlet of the retentate, as an end point. As a result, the direction of flow of the retentate runs substantially parallel to the flow path along the flat filter material, i.e., in essence without deflections, so that a stable and reliable flow of the retentate can be ensured by the crossflow filtration unit. In addition, due to the substantially linear flow path without deflections, loops or the like, it is possible to minimize the pressure drop in the filtration unit as well as undesired effects of non-linear flows on the target substances, contained in the feed fluid. For the above reasons it is also preferred that the inlet for the diafiltration medium be mounted in the first edge region of the crossflow filtration unit. However, it is also possible to mount the inlet for the diafiltration medium in the second edge region or in the third and/or fourth edge region.

According to a preferred embodiment of the invention, the outlet for the permeate is mounted in the second edge region of the crossflow filtration unit. It is particularly preferred that in each case at least one outlet for the permeate be mounted in both the first and the second edge region of the crossflow filtration unit. In another embodiment of the invention the outlets for the permeate are mounted, as an alternative or in addition, in the third and/or fourth edge region of the crossflow filtration unit. The third edge region is located on the left side of the flow direction in a plan view of the crossflow filtration unit from the side of the diafiltration channel. Correspondingly the fourth edge region is located on the right side and, thus, lies opposite the third edge region. The above arrangement of the outlet(s) makes it possible to achieve not only a particularly high permeate performance, but also design advantages.

The first edge region comprises preferably the outer third of the length of the filtration unit opposite to the direction of flow. Correspondingly the second edge region comprises the outer third of the length of the filtration unit along the direction of flow. The same applies to the third and fourth edge regions. It is advantageous to make the first to fourth edge regions as small as possible. Therefore, it is particularly preferred that the edge regions comprise the respective outer 20%, even more preferably the respective outer 10%, and most preferably the respective outer 3%.

In principle, there is no particular constraint on the mounting of the inlets and outlets. For example, the inlets and outlets may be mounted in such a way that the feed fluid already enters the retentate channel in the direction of flow and leaves it in the direction of flow. Correspondingly the outlet for the permeate can be mounted in such a way that the permeate leaves the permeate collection channel in the direction of flow; and/or the inlet for the diafiltration medium can be mounted in such a way that it enters the diafiltration channel in the direction of flow. Preferably, however, the inlets and outlets are mounted in such a way that the diafiltration medium enters the diafiltration channel perpendicular to the direction of flow; and then the feed fluid enters the retentate channel perpendicular to the direction of flow and leaves it, as a retentate, perpendicular to the direction of flow. Such a mounting of the inlets and outlets facilitates the arrangement of a plurality of the inventive filtration units to form a filter cassette.

Preferably the crossflow filtration unit comprises a plurality of inlets for the feed fluid, a plurality of outlets for the retentate, and a plurality of outlets for the permeate.

In a preferred embodiment the free volume of the diafiltration channel and/or the retentate channel (space available for the diafiltration medium/the retentate, the dead volume or void volume) decreases in the direction of flow from the inlet for the feed fluid to the outlet for the retentate. Due to the decreasing volume(s) and the flatness of the filter materials, the crossflow filtration unit has a low pressure loss and a substantially deflection-free flow path of the diafiltration medium and the retentate. This aspect makes it possible to increase the output per unit area of the crossflow diafiltration unit and to operate the crossflow diafiltration unit in the "single pass" mode (only a single passage of the retentate takes place without recycling).

In another preferred embodiment of the invention the decrease in the free volume along the direction of flow is implemented by decreasing the width of the diafiltration channel and/or the width of the retentate channel in the direction of flow. The width extends along the flat first filter material and perpendicular to the direction of flow. It is particularly preferred that the width of the entire crossflow filtration unit decrease in the direction of flow. The retentate channel or, more specifically, the crossflow filtration unit is preferably trapezoidal in a plan view along a normal of the plane, in which the flat first filter material is located. The basic trapezoidal shape of the diafiltration channel and/or the retentate channel or, more specifically, the crossflow filtration unit can have unequal sides, for example, may be right angled and is preferably equal sided.

According to an embodiment, the height of the diafiltration channel and/or the retentate channel or, more specifically, the crossflow filtration unit may decrease in the direction of flow. For example, the diafiltration channel and/or the retentate channel may be wedge-shaped. The height of the diafiltration channel and/or the retentate channel or, more specifically, the crossflow filtration unit is perpendicular to the flat first filter material and perpendicular to the direction of flow.

There is no particular constraint on the width, length and height of the crossflow filtration unit. The length runs parallel to the direction of flow and along the flat first filter material. Preferably the crossflow filtration unit has a length of at least 50 mm, preferably at least 150 mm, more preferably 500 mm, most preferably 750 mm or more. Such a length can be achieved, for example, by connecting several, for example, at least 2, at least 3 or at least 4, crossflow filtration units in series. Due to a longer length, a particularly high efficiency can be achieved.

In a preferred embodiment of the invention the free volume of the permeate collection channel changes in the direction of flow. It is particularly preferred that the free volume of the permeate collection channel decrease in the direction of flow. This aspect makes it possible to retain, for example, the outer dimensions of the filtration cassette.

The explanations regarding the configuration of the retentate channel apply to the corresponding permeate collection channel and vice versa.

"Free volume decreasing in the direction of flow" means that there exists a cross sectional area $A_1$, through which the diafiltration medium or the retentate can flow and which is located in a plane, which has a normal parallel to the direction of flow, and a corresponding cross sectional area $A_2$, which is parallel to $A_1$ and is further away from the inlet for the diafiltration medium or the feed fluid than $A_1$, wherein the surface area $A_1$, through which the diafiltration medium or the retentate can flow, is greater than $A_2$; and there are no correspondingly defined planes $A_1'$ and $A_2'$, for which the surface area of $A_1'$ is smaller than that of $A_2'$.

The decrease in the free volume can be continuous (for all $A_1$ and $A_2$ it holds that $A_1 \geq A_2$) or continuous (for all $A_1$ and $A_2$ it holds that $A_1 > A_2$). It is also possible that the decrease in volume is discontinuous. That means that at least one discontinuous drop or crack in the cross sectional area occurs along the direction of flow.

The change in the free volume of the retentate channel in the direction of flow is preferably in the range of 20 to 1 to 1.2 to 1, preferably at 10 to 1, depending on the filtration task. In this case the "change in the free volume of the retentate channel in the direction of flow" refers to the ratio of the cross sectional area $A_1$ at the inlet for the feed fluid to the cross sectional area $A_2$ at the outlet for the retentate.

In an embodiment of the invention the thickness of the diafiltration channel and/or the thickness of the retentate channel and optionally the thickness of the permeate collection channel decreases/decrease in the direction of flow.

The diafiltration channel, the retentate channel and the permeate collection channel are usually kept open by spacers for the respective media. In a preferred embodiment of the invention a flat spacer is mounted in the diafiltration channel and/or in the retentate channel of the crossflow filtration unit in such a way that the free volume of the retentate channel decreases in the direction of flow.

Suitable spacers for crossflow filtration units are known in the prior art and may be used in the diafiltration channel, retentate channel and/or permeate collection channel of the crossflow filtration unit according to aspects of the present invention. According to aspects of the invention, the spacers are modified preferably in such a way that their volume in the direction of flow increases in order to achieve a decrease in the volume of the free volume available for the diafiltration medium or the retentate. Preferred spacers may be textile materials of organic or non-organic materials, such as woven fabrics, knitted fabrics, non-woven fabrics or extruded nets.

The spacer may be advantageously a non-planar plate. The non-planar plate may be a plate that has at least one non-planar main surface. The main surfaces of a plate are the opposing surfaces having the largest surface area. The at least one non-planar main surface may have unevenness in the form of a corrugated or serrated surface. In addition, the uneven surface may have protruding elements, such as cones (frustums of cones), pyramids (frustums of pyramids), burls or other geometric shapes. The non-planar plate can also be similar to a corrugated sheet in a corrugated or serrated shape, with the undulations or serrations extending preferably parallel to the direction of flow. Suitable materials for the non-planar plate are the same as those listed below for spacers in the form of an open-mesh matrix.

According to a preferred embodiment, the spacer consists of an open-mesh matrix or of an extruded net. Such spacers are known in the prior art and have been described, for example, in the publication of the German patent application DE 100 22 259 A1. As already mentioned above, the spacers according to aspects of the present invention are modified preferably in such a way that their volume increases in the direction of flow, in order to achieve a decrease in the volume of the free volume available for the diafiltration medium or the retentate. In principle, conventional spacers can also be installed in the crossflow filtration unit according to aspects of the invention, for example, in the permeate collection channel and/or in the diafiltration channel or in all of the channels of the filtration unit having a width that decreases in the direction of flow. A decreasing width can be achieved, as described above, for example, with a trapezoidal configuration of the channels or, more specifically, the crossflow filtration unit.

In one embodiment the mesh width of the open-mesh matrix or the extruded net can decrease in the direction of flow, in order to achieve a decrease in the free volume along the direction of flow. For example, the mesh number at the inlet for the diafiltration medium or at the inlet for the feed fluid ranges from 5/cm to 15/cm; in the middle between the inlet for the diafiltration medium or the inlet for the feed fluid and the outlet for the retentate, 10/cm to 30/cm; and at the outlet for the retentate, 20/cm to 40/cm.

As an alternative or in addition, the open-mesh matrix or the extruded net can be constructed from intersecting longitudinal and transverse threads; and the number and/or thickness of the longitudinal and/or transverse threads can increase in the direction of flow. The open-mesh matrix consists preferably of an organic polymer, such as, for example, polypropylene, polyethylene, polyester, polyvinyl chloride or polyvinylidene fluoride or blends thereof. Furthermore, it is possible that the open-mesh matrix is constructed from fibers of different types of polymers.

In an additional preferred embodiment of the invention several layers of textile materials are arranged one above the other in the retentate channel in such a way that the free channel volume decreases in the direction of flow. This aspect can be achieved, for example, in that the layers, which are disposed one above the other, begin so as to be offset in the direction of flow. The superimposed layers extend preferably up to the second edge region. As a result, an increasing volume is used by the textile materials in the retentate channel in the flow direction, so that the free volume decreases in the direction of flow. The textile materials, such as woven fabrics, knitted fabrics, non-woven fabrics or extruded nets, may consist of organic or non-organic materials.

The embodiments, shown herein, for realizing the decrease in the free volume of the diafiltration channel or the retentate channel can be combined in any arbitrary way.

According to aspects of the invention, the retentate channel is bounded by a flat first filter material and a flat second filter material. The diafiltration channel is bounded by at least one flat first filter material. The permeate collection channel is bounded by at least one flat second filter material. Adjacent to a retentate channel are a diafiltration channel and a permeate collection channel. A preferred crossflow filtration unit of the invention comprises a plurality of stacked arrays of diafiltration channel, flat first filter material, retentate channel, flat second filter material, permeate collection channel, flat second filter material, retentate channel and flat first filter material, preferably sealed by another diafiltration channel, so that the stacked arrays are combined to form one filter cassette. Suitable embodiments for filter cassettes are known in the prior art. Preferably each diafiltration channel of these arrays is delimited from two retentate channels on both sides by a respective filter material, which corresponds to the first filter material. Each permeate collection channel of these arrays is delimited from two retentate channels on both sides by a respective filter material, which corresponds to the second filter material. The first filter materials and second filter materials may each be different from one another. Fundamentally different first filter materials and different second filter materials can be used. Preferably similar first filter materials and/or similar second filter materials are used.

According to a preferred embodiment, the flat first and second filter materials have, independently of one another, a substantially uniform thickness of preferably 50 μm to 10,000 μm, more preferably 150 μm to 1,000 μm. If the flat delimitation of the diafiltration channel using the flat first filter material and the further flat delimitation of the diafiltration channel and/or the flat delimitations of the retentate channel using the first and second filter material do not run parallel to one another, then the free volume of the diafiltration channel and/or the retentate channel can be designed so as to be wedge-shaped, so that the free volume decreases in the direction of flow. It is particularly preferred that the diafiltration channel, the retentate channel and the permeate collection channel be bounded on both sides by substantially parallel surfaces.

The shape of the crossflow filtration unit is not subject to any particular constraint. The crossflow filtration unit may be, for example, cuboid or cylindrical.

In another aspect, an embodiment of the present invention relates to a method for diafiltration of a feed fluid, in order to obtain a retentate and a permeate, said method comprising the steps of:
  (A) providing a crossflow filtration unit;
  (B) feeding a diafiltration medium into the inlet for the diafiltration medium;
  (C) feeding the feed fluid into the inlet for the feed fluid;
  (D) discharging the retentate from the outlet for the retentate; and
  (E) discharging the permeate from the outlet for the permeate.

The explanations with respect to the crossflow filtration unit and the diafiltration method are mutually applicable to both.

Step (A) provides preferably the above-described crossflow filtration unit, which comprises a plurality of stacked arrays of diafiltration channel, flat first filter material, retentate channel, flat second filter material, permeate collection channel, flat second filter material, retentate channel and flat first filter material so that the stacked arrays are combined to form a filter cassette.

The diafiltration medium that is used is not subject to any particular constraint. In principle, any fluid is suitable, with water and aqueous salt solutions being preferred. Special preference is given to an aqueous buffer solution as the diafiltration medium.

Preferably the volume flow rate of the supplied diafiltration medium is 0.1 to 15 times the volume flow rate of the supplied feed fluid. The volume flow rate of the discharged retentate is preferably 0.05 to 10 times the volume flow rate of the supplied feed fluid.

In a preferred embodiment of the method, the diafiltration medium is supplied at a pressure of 0.1 to 4 bar. More preferably, the diafiltration medium is supplied at a pressure that is greater than the retentate outlet pressure.

Preferably the method according to aspects of the present invention is carried out continuously, i.e., under constant/continuous addition of the diafiltration medium and the feed fluid, so that a particularly efficient and economical filtration method can be provided. According to aspects of the invention, "continuous diafiltration" refers to a diafiltration method, in which both the diafiltration medium and the feed fluid are added continuously.

In a preferred embodiment of the method a plurality of inventive and independent crossflow filtration units are provided in step (A) and are connected in series in such a way that the outlet for the retentate of the respective upstream crossflow filtration unit is connected in a fluid conducting manner to the inlet for the feed fluid of a downstream crossflow filtration unit. In this embodiment, moreover, in step (C) the feed fluid is fed into the inlet for the feed fluid of that crossflow filtration unit, which is not preceded by any other crossflow filtration unit (first crossflow filtration unit), and in step (D) the retentate from the outlet for the retentate of that crossflow filtration unit, which is not followed by any other crossflow filtration unit (last crossflow filtration unit). In this way the retentate/the feed fluid passes through the series-connected crossflow filtration units from the first to the last unit. Preferably 2 to 10, more preferably 2 to 5 crossflow filtration units are connected in series. The diafiltration medium in this embodiment is fed separately to each of the series-connected crossflow filtration units. While it is possible to use different types of diafiltration media, it is preferred to feed the same diafiltration medium to each of the crossflow filtration units. Preferably each of the series-connected crossflow filtration units is, as described above, in the form of a filter cassette.

In a preferred embodiment of the method a plurality of inventive and independent crossflow filtration units are provided in step (A) and are connected in parallel. Both the parallel connection and the series connection can be combined with each other.

In an additional preferred embodiment of the method the retentate, which was discharged in step (D), is led back at least partially into the inlet for the feed fluid. Owing to the recycling process an improved result of the process can be achieved, in the event that a single pass through the crossflow filtration unit is not sufficient. In this case the addition of the diafiltration fluid and the removal of the permeate take place without recycling. If a plurality of crossflow filtration units are connected in series, then, in principle, any retentate flow can be resupplied to each inlet for the feed fluid. Preferably in this case the retentate of each individual crossflow filtration unit is led back to the inlet for the feed fluid of the same crossflow filtration unit.

According to another preferred embodiment of the method according to aspects of the invention, the feed fluid or the retentate in the retentate channel is set in oscillation. As a result, the flow motion in the retentate channel is overlaid by an oscillation (oscillation). This may be accomplished by at least one device that is intended for generating oscillation and that can be mounted on the feed fluid inlet and/or on the retentate outlet. Such a device for generating oscillation moves the retentate back and forth in the retentate channel. That means that the retentate is set in oscillating motion that runs substantially parallel to the flat first filter material. Preferably the oscillation is generated by an oscillation generating device, mounted at the feed fluid inlet, and another oscillation generating device, mounted at the retentate outlet. An oscillation generating device that is suitable according to the invention is, for example, a piston pump. A device for generating oscillation comprises preferably a reservoir, which is divided into two halves by an elastic membrane, and optionally a pressure source. The reservoir is a reservoir (storage) for the feed fluid or the retentate. The first half of the reservoir is connected by a valve controller to a pressure source, such as, for example, a compressed air source or a pump. The second half of the reservoir is connected in a fluid conducting manner to the feed fluid inlet or the retentate outlet of the filtration apparatus. In the second half there is also preferably a purging valve or bleed valve. Due to the opposing (alternating) pressurization of each one of the first halves of the two reservoirs (for example, with compressed air) the retentate flow can be moved back and forth (set in oscillation). The reservoirs, described above, can be both a separate part of the system (not part of the crossflow filtration unit) as well as be integrated, as part of the crossflow filtration unit, in the housing thereof.

The crossflow filtration unit according to aspects of the present invention has preferably at least one (preferably two) device(s) for generating an oscillation of the feed fluid or the retentate in the retentate channel. It is preferred according to aspects of the invention that a device for generating oscillation comprise a reservoir with a pressure source. It is particularly preferred that the crossflow filtration unit of the present invention comprise a first reservoir, optionally with a first pressure source, and a second reservoir, optionally with a second pressure source, wherein the first reservoir is connected in a fluid conducting manner to the inlet for the feed fluid and the second reservoir is connected in a fluid conducting manner to the outlet for the retentate, provided that at least one of the first and second pressure sources is present. Preferably both the first and the second reservoir each have a pressure source. Each of the reservoirs is divided preferably into two halves by an elastic and fluid impermeable (gas and liquid impermeable) membrane, with the first half being connected to a pressure source. The second half of the first reservoir is connected preferably in a fluid conducting manner to the inlet for the feed fluid. The second half of the second reservoir is connected preferably in a fluid conducting manner to the outlet for the retentate.

According to a preferred embodiment, the method according to aspects of the present invention further comprises the step (C0) of separating a pre-feed fluid into a pre-retentate and a pre-permeate. This upstream step allows a fluid to be concentrated first, for example, by filtration or diafiltration, and/or to be (partially) freed of impurities, in order to be then subjected to a subsequent diafiltration using the crossflow filtration unit of the present invention. If step (C0) is a filtration step or diafiltration step, then, in principle, both the pre-retentate and the pre-permeate can be used as the feed fluid, but preferably the pre-retentate from step (C0) is used.

Step (C0) is advantageously carried out using a crossflow filtration unit (C0 unit) to separate a pre-feed fluid into a pre-retentate and a pre-permeate. Such crossflow filtration units are known in the prior art. In this case the C0 unit can be upstream of the first crossflow filtration unit, as described above for the series connection of the crossflow filtration units according to aspects of the present invention.

It is particularly advantageous to have, as a C0 unit, a crossflow filtration unit, comprising a pre-retentate channel, a flat filter material and a pre-permeate collection channel, arranged in such a way that the flat filter material delimits the pre-retentate channel and the pre-permeate collection channel from each other, wherein the pre-retentate channel is connected in a fluid conducting manner to at least one inlet for the pre-feed fluid and is connected to at least one outlet for the pre-retentate; and the pre-permeate collection channel is connected in a fluid conducting manner to at least one outlet for the pre-permeate; the inlet for the pre-feed fluid is mounted in a first edge region of the crossflow filtration unit; and the outlet for the pre-retentate is mounted in a second edge region of the crossflow filtration unit, with said second edge region being located opposite the first edge region; and preferably the free volume of the pre-retentate channel decreases in the flow direction from the inlet for the pre-feed fluid to the outlet for the pre-retentate. Owing to the decrease in the free volume in the direction of flow it is possible to provide a C0 unit having a low pressure loss and a high utilization of the surface area.

The explanations with respect to the crossflow filtration unit of the present invention for diafiltration and, in particular, the explanations with respect to the retentate channel and the permeate collection channel thereof apply correspondingly to the design of the C0 unit and, in particular, the pre-retentate channel and the pre-permeate collection channel. The flat filter material of the C0 unit may be a microfiltration membrane and preferably an ultrafiltration membrane. Like the crossflow filtration unit of the present invention, the C0 unit may be expanded into a filter cassette.

The method according to aspects of the present invention is carried out preferably under the following conditions:

$$P_{DF} \geq P_{retentate} \quad (F)$$

$$x = V_{DF}/V_{feed}, \text{ preferably } x \geq 1, \text{ more preferably 3 to 10; and} \quad (G)$$

$$k = V_{feed}/V_{retentate}, \text{ preferably } k \geq 1; \quad (H)$$

where
$P_{DF}$ is the pressure, at which the diafiltration medium is added;
$P_{retentate}$ is the retentate outlet pressure, i.e., the pressure, at which the retentate leaves the filtration apparatus;
$V_{retentate}$ is the volume flow rate of the retentate;
$V_{DF}$ is the volume flow rate of the diafiltration medium;
$V_{feed}$ is the volume flow rate of the feed fluid;
x is the so-called DF ratio and
k is the so-called concentration factor.

The method according to aspects of the present invention is particularly suitable for filtration, diafiltration, concentration and/or modification of the ion composition of a protein solution or combinations thereof.

The method according to aspects of the present invention may be a part of a more extensive procedure. For example, the diafiltration process may follow a pre-treatment and/or precede an aftertreatment. Some examples of suitable pre-treatments or aftertreatments include reaction of educts to form products by biological or chemical means, thermal and mechanical separation methods and chemical analysis methods.

In a further aspect, an embodiment of the present invention relates to an apparatus for carrying out a chemical or biological process, said apparatus comprising the crossflow diafiltration unit described above. Such an apparatus may comprise, for example, a bioreactor, a unit for cell separation, a unit for diafiltration with the crossflow diafiltration unit of the present invention, and a unit for chromatography. Suitable chemical and biological processes are, for example, the production of vaccines or biopharmaceuticals.

Moreover, aspects of the present invention relate to the use of the crossflow filtration unit for continuous diafiltration within a chemical or biological process, wherein the step of continuous diafiltration is preceded by at least one conditioning step for the feed fluid and/or is followed by at least one post-conditioning step for the retentate. Suitable conditioning and post-conditioning steps are, for example, reaction in a bioreactor, optionally followed by cell separation, chromatography, filtration, concentration and dilution (see FIG. 4).

Aspects of the present invention are explained in the context of, but are not limited to, the following examples.

Example 1

A solution of albumin and NaCl (5.2% by weight of albumin in 0.9% by weight of an aqueous NaCl solution) was subjected to diafiltration. The determination of the albumin concentration was carried out photometrically at a wavelength of the light of 280 nm. The conductivity of the starting solution was 14 mS. Demineralized water was used as the diafiltration medium.

The diafiltration unit was designed as a filter cassette, wherein 13 arrays of diafiltration channel, flat first filter material, retentate channel, flat second filter material, permeate collection channel, flat second filter material, retentate channel and flat first filter material were stacked one above the other and supplemented by an additional diafiltration channel. A Hydrosart® membrane of the 10 kDa type from Sartorius Stedim Biotech GmbH was used as the flat second filter material. A polyethersulfone membrane of the 30 kDa type from Sartorius Stedim Biotech GmbH was used as the flat first filter material. The DF ratio (volume of diafiltration medium/volume of feed fluid) was about 5.5:1.

For the duration of the test period the settings of the pumps and valves were not readjusted. The diafiltration unit operated with stable performance. The low conductivity of the retentate of 2.2 mS indicates that superior diafiltration performance was achieved.

The result of the above example is shown in the following Table 1.

TABLE 1

| Time (min.) | $P_{feed}$ (bar) | $P_{retentate}$ (bar) | $P_{DF}$ (bar) | $V_{feed}$ (ml/min.) | $V_{retentate}$ (ml/min.) | $V_{permeate}$ (ml/min.) | $C_{protein}$ (% by wt.) | X (vol./vol.) | $LF_{permeate}$ (mS) | $LF_{retentate}$ (mS) | T (° C.) |
|---|---|---|---|---|---|---|---|---|---|---|---|
| 0 (start) | 2.42 | 0.77 | 1.8 | 14.6 | 12.8 | 80.8 | 5.6 | 5.5:1 | 2.5 mS | 2.25 mS | approx. 20° C. |
| 30 min. | 2.40 | 0.77 | 1.8 | 14.6 | 14.3 | 82.0 | 4.96 | 5.5:1 | 2.4 mS | 2.18 mS | approx. 20° C. |
| 60 min. | 2.39 | 0.77 | 1.8 | 14.6 | 14.6 | 81 | 5.1 | 5.5:1 | 2.4 mS | 2.18 mS | approx. 20° C. |

$P_{feed}$ pressure, at which the feed fluid is added
$P_{retentate}$ retentate outlet pressure
$P_{DF}$ pressure, at which the diafiltration medium is added
$V_{feed}$ volume flow rate of the feed fluid
$V_{retentate}$ volume flow rate of the retentate
$V_{permeate}$ volume flow rate of the permeate
$C_{protein}$ concentration of albumin (percentages by weight)
x DF ratio (volume of diafiltration medium/volume of feed fluid)
$LF_{permeate}$ conductivity of the permeate
$LF_{retentate}$ conductivity of the retentate
T temperature

Example 2

A solution of approximately 22 g/l of albumin (1 g/l corresponds to 0.1% by wt.) in 10 millimolar KPi buffer (10 mmol/l of potassium dihydrogen phosphate and 10 mmol/l of dipotassium hydrogen phosphate) and 0.9% by wt. of NaCl was subjected to diafiltration. The determination of the albumin concentration was carried out photometrically at a wavelength of the light of 280 nm. The conductivity of the starting solution was 15.9 mS. The diafiltration medium (DF) that was used was a 10 millimolar KPi solution having a conductivity of 2.05 mS.

The diafiltration units that were used were designed as a filter cassette, with each of the diafiltration units having 8 arrays of diafiltration channel, flat first filter material, retentate channel, flat second filter material, permeate collection channel, flat second filter material, retentate channel and flat first filter material stacked one above the other and supplemented by an additional diafiltration channel. A Hydrosart® membrane of the 10 kDa type from Sartorius Stedim Biotech GmbH was used as the flat second filter material. A Hydrosart® membrane of the 30 kDa type from Sartorius Stedim Biotech GmbH was used as the flat first filter material.

In this example three of the diafiltration units described above were connected in series using deflecting plates for the feed fluid in such a way that the feed fluid was passed serially through all three cassettes. In contrast, the diafiltration fluid was passed in parallel into all three diafiltration units.

The total filter area of all three flat second filter materials was 0.2 m². The DF ratio (volume diafiltration medium/volume of feed fluid) was about 4.5:1.

The result of the above example is shown in the following Table 2.

For the duration of the test period the settings of the pumps and valves were not readjusted.

The diafiltration unit operated for a period of 2 hours with constant and stable performances.

The effectiveness of the diafiltration was calculated from the decrease in the conductivity (LF) in the feed stream and is referred to in the table as "clearance". The calculation of the clearance in percentage was carried out according to the formula:

$$\text{Clearance} = 100 - ((LF_{retentate} - LF_{DF})/(LF_{feed} - LF_{DF}) * 100),$$

where LF is the conductivity of each medium.

The clearance value that was calculated in this way was compared with the theoretically achievable value.

The calculation of the theoretically achievable clearance was carried out according to the formula:

$$\text{theoretically achievable clearance} = 100 - ((1/e)^n \cdot 100)$$

where e is the Euler number, and n denotes the DF ratio.

Example 2 shows that an extremely effective continuous diafiltration, which can reach the theoretical (maximum possible) clearance value of 99%, is possible with the apparatus according to aspects of the invention.

In this respect it must be noted that when diluted with 4.5 times the amount of diafiltration solution mentioned in the example and a subsequent concentration of the protein solution to the original volume according to the known prior art, a clearance value of only 78% can be achieved. Even a successive addition in 5 individual steps, each with a subsequent concentration to the starting volume, would yield a clearance value of only 96%. Even this value is still significantly below the clearance of 99% that can be achieved according to aspects of the invention.

TABLE 2

| Time (min.) | $P_{feed}$ (bar) | $P_{retentate}$ (bar) | $P_{DF}$ (bar) | $V_{feed}$ (ml/min.) | $V_{retentate}$ (ml/min.) | $V_{permeate}$ (ml/min.) | $C_{protein}$ (g/l) | X (vol./vol.) | $LF_{retentate}$ (mS) | Clearance % | Clearance theoretically % | T (° C.) |
|---|---|---|---|---|---|---|---|---|---|---|---|---|
| 5 min. | 1.07 | 1.08 | 1.2 | 20 | 20 | 90 | 21.3 | 4.5 | 2.28 | 99 | 99 | approx. 19° C. |
| 15 min. | 1.09 | 1.02 | 1.2 | 22 | 20 | 90 | 22.4 | 4.5 | 2.18 | 99 | 99 | approx. 19° C. |
| 30 min. | 1.07 | 1.01 | 1.19 | 22 | 20 | 88 | 21.5 | 4.5 | 2.17 | 99 | 99 | approx. 19° C. |
| 60 min. | 1.03 | 0.97 | 1.14 | 21.5 | 20 | 88 | 23.6 | 4.5 | 2.14 | 99 | 99 | approx. 19° C. |
| 90 min. | 1.01 | 0.95 | 1.12 | 21 | 20 | 88 | 25 | 4.5 | 2.16 | 99 | 99 | approx. 19° C. |
| 120 min. | 1.00 | 0.95 | 1.12 | 22 | 20 | 88 | 22.5 | 4.5 | 2.16 | 99 | 99 | approx. 19 C. |

$P_{feed}$ pressure, at which the feed fluid (feed) is added
$P_{retentate}$ retentate outlet pressure
$P_{DF}$ pressure, at which the diafiltration medium is added
$V_{feed}$ volume flow rate of the feed fluid
$V_{retentate}$ volume flow rate of the retentate
$V_{permeate}$ volume flow rate of the permeate
$C_{protein}$ concentration of albumin (g/l)
x DF ratio (volume of diafiltration medium/volume of feed fluid)
$LF_{retentate}$ conductivity of the retentate
Clearance decrease in conductivity in percent (100% = maximum possible decrease in conductivity)
Clearance theoretically maximum possible decrease in conductivity in percent
T temperature

BRIEF DESCRIPTION OF THE DRAWINGS

FIG. 5A shows a crossflow diafiltration unit with a bioreactor and a cell separation unit positioned upstream and a chromatography unit/a chromatography step positioned downstream of the crossflow diafiltration unit. The embodiment shown in FIG. 5B shows a crossflow diafiltration unit preceded by a chromatography step and followed by a chromatography step, and the embodiment shown in FIG. 5C shows a crossflow diafiltration unit positioned before a final filtration step.

DETAILED DESCRIPTION

Figure 1:
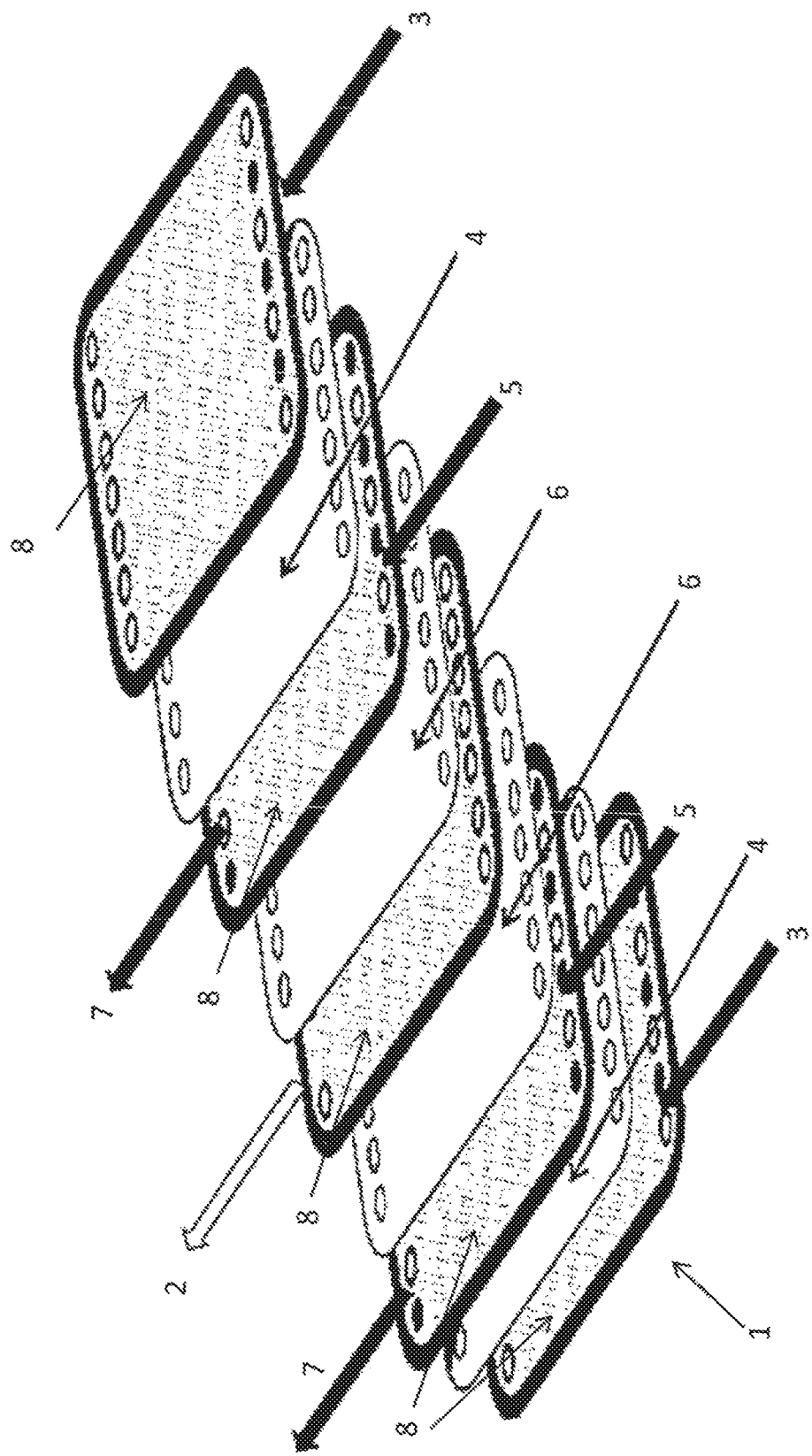
FIG. 1 shows an example structure of a crossflow diafiltration unit according to embodiments provided herein.

FIG. 1 shows a possible structure of a crossflow diafiltration unit (1) according to aspects of the invention with a flat second filter material in the form of an ultrafiltration membrane (6) and a flat first filter material in the form of a microfiltration membrane (4), wherein the streams of diafiltration medium (3), feed fluid (5), retentate (7) and permeate (2) are illustrated by arrows. The diafiltration channel, the retentate channel and the permeate collection channel are kept open by spacers (8) for the respective media.

Figure 2:
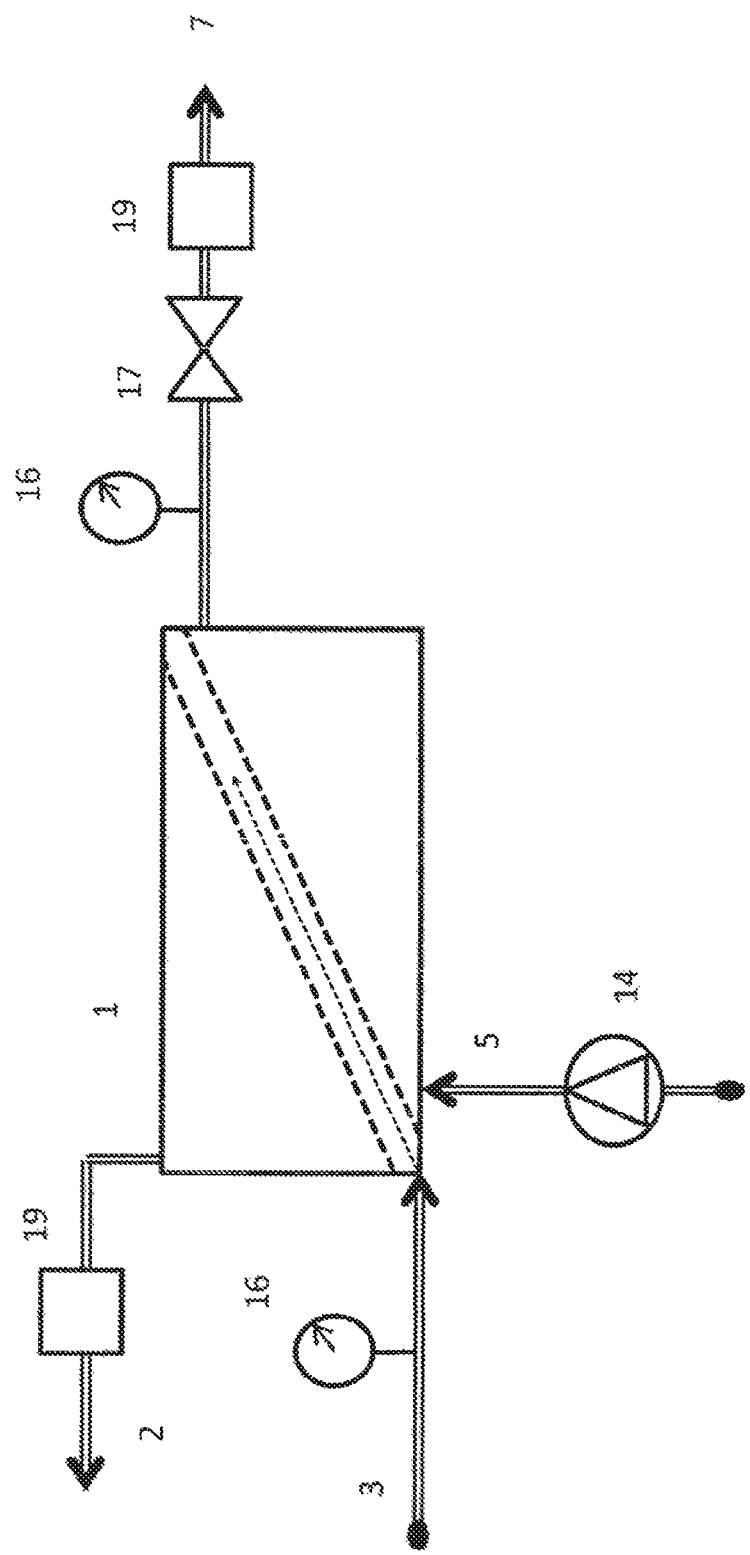
FIG. 2 is a schematic of an example diafiltration process carried out with a crossflow diafiltration unit according to embodiments provided herein.

FIG. 2 shows in schematic form an example of how the diafiltration process according to aspects of the present invention is carried out with a crossflow diafiltration unit that is designed as a diafiltration cassette (1). In this case the feed fluid (5) is supplied by a pump (14) at the inlet for the feed fluid. In front of the inlet for the diafiltration medium and after the outlet for the retentate, the pressure of the diafiltration medium (3) or the retentate (7) is measured by manometers (16). The respective composition of the retentate (7) and the permeate (2) is monitored by a measuring device, for example, a conductometer (19). The volume flow rate of the retentate (7) is controlled by a throttle valve (17).

Figure 3:
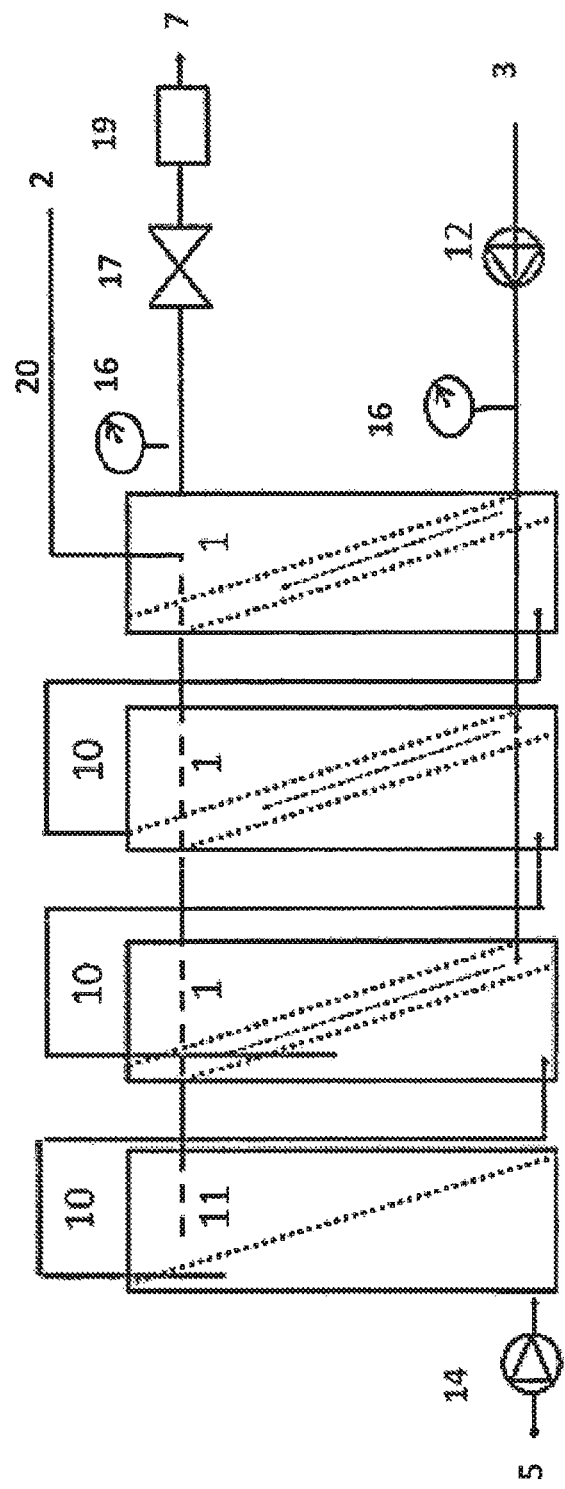
FIG. 3 is a schematic of an example diafiltration process using three diafiltration cassettes connected in series according to embodiments provided herein.

FIG. 3 shows in schematic form an example of how the diafiltration process according to aspects of the present invention is carried out, wherein three diafiltration cassettes (1) are connected in series. Upstream there is a step of separating a fluid into a pre-retentate and a pre-permeate using a conventional crossflow filtration cassette (11). The feed fluid (5) is supplied with a pump (14). The diafiltration medium (3) is fed to the three diafiltration cassettes (1) with a pump (12). The pre-retentate from the respective upstream filtration unit is fed through a channel (10) to the respective downstream filtration unit as a feed fluid. In front of the inlet for the diafiltration medium and after the outlet for the retentate, the pressure of the diafiltration medium (3) or the retentate (7) is measured by manometers (16). The composition of the retentate (7) is monitored by a measuring device, for example, a conductometer (19). The volume flow rate of the retentate (7) is controlled by a throttle valve (17). The permeate (2) from all of the modules (11, 1) is discharged through the collection line (20).

Figure 4:
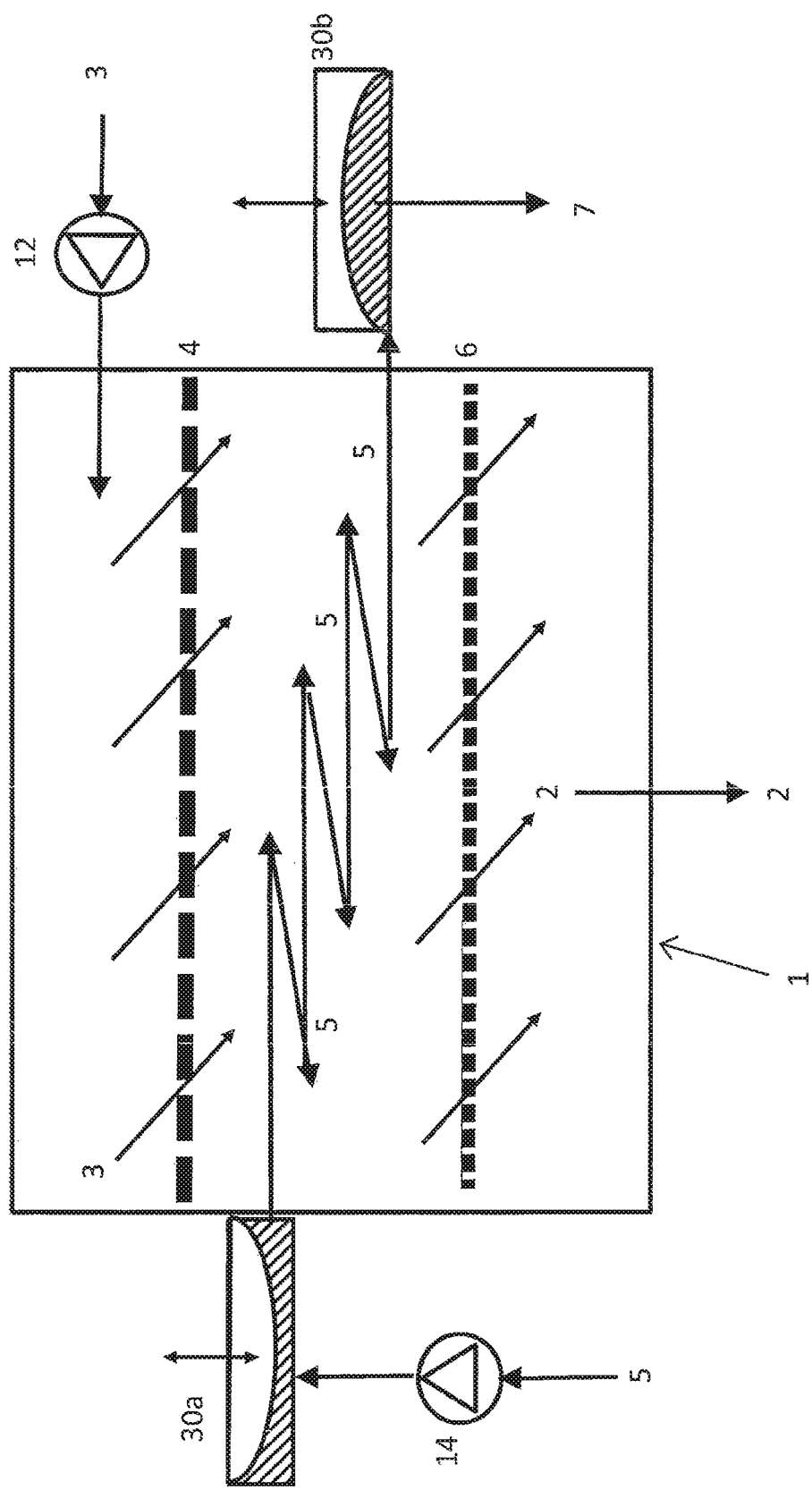
FIG. 4 is a schematic of an example diafiltration process using a crossflow diafiltration unit, wherein the feed fluid/the retentate is/are oscillated in the retentate channel according to embodiments provided herein.

FIG. 4 shows in schematic form an example of how the diafiltration process according to aspects of the present invention is carried out as well as a crossflow diafiltration unit of the present invention, wherein the feed fluid/the retentate (5) is/are oscillated in the retentate channel. The feed fluid (5) is introduced with a pump (14) into a reservoir (30a) and subsequently into the retentate channel. Thereafter, the feed fluid/the retentate (5) passes/pass through a second device for generating oscillation or a second reservoir (30b). The diafiltration medium (3) is introduced with a pump (12) into the diafiltration channel. The illustrated crossflow diafiltration unit has two devices for generating oscillation, with the first device comprising a first reservoir (30a) and the second device comprising a second reservoir (30b) that is different from said first one. The reservoir (30a) is connected in a fluid conducting manner to the inlet for the feed fluid (5). The reservoir (30b) is connected in a fluid conducting manner to the outlet for the retentate (7). Each reservoir is separated into two halves by an elastic and fluid impermeable membrane. The first half of the first reservoir (30a) (shown with non-hatched region in FIG. 4) is connected to a pressure source through a valve controller. The second half of the first reservoir (30a) (shown with hatched region in FIG. 4) is connected in a fluid conducting manner to the inlet for the feed fluid. The second reservoir (30b) is separated into two halves by an elastic and fluid impermeable membrane. The first half of the second reservoir (30b) (shown with non-hatched region in FIG. 4) is connected to a pressure source through a valve controller. The second half of the second reservoir (30b) (shown with a hatched region in FIG. 4) is connected in a fluid conducting manner to the outlet for the retentate. By controlling or regulating the pressure level of the compressed air (opposing application of compressed air on the respective first half of 30a and 30b) an oscillating motion of the feed fluid/the retentate is generated in the retentate channel. Part of the retentate is continuously discharged, in order to ensure a continuous process.

FIG. 5 shows examples of various sections A to C of the process schematics for carrying out a method for producing biopharmaceuticals, wherein each of the processes comprises the provision of at least one crossflow diafiltration unit (1) of the present invention. The dashed square brackets and the preceding or following arrows indicate that further process steps can be upstream or downstream.

Figure 5A:
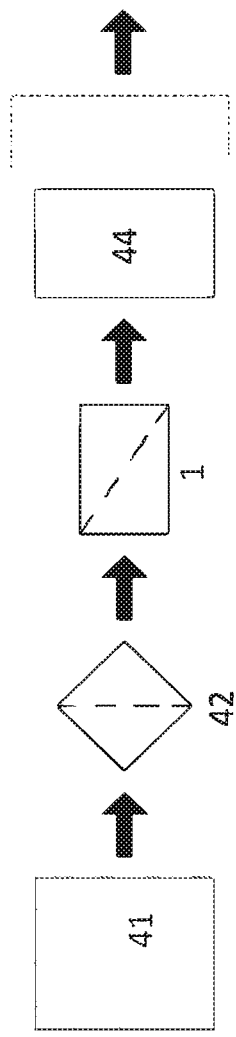
FIGS. 5A-5C show various examples of processes using a crossflow diafiltration unit, according to the embodiments provided herein.

The embodiment, shown in FIG. 5A, comprises a crossflow diafiltration unit (1) of the invention, wherein a bioreactor (41) and a cell separation unit (42) are located upstream. Downstream of the crossflow diafiltration unit (1) there is a chromatography unit/a chromatography step (44). The flow of the product solution from the bioreactor (1) is illustrated by arrows.

Figure 5B:
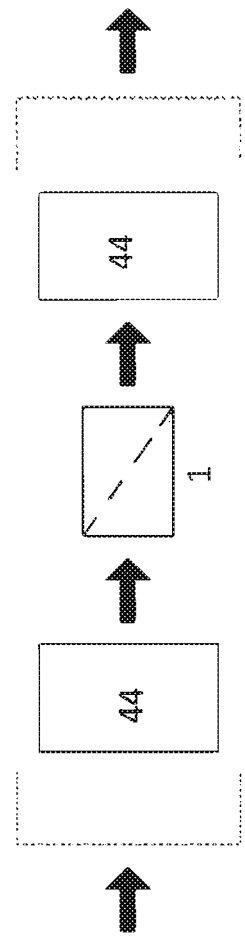

The embodiment, shown in FIG. 5B, comprises a crossflow diafiltration unit (1) of the invention between two chromatography steps (44). That means that the diafiltration is preceded by a chromatography step and followed by a chromatography step.

Figure 5C:
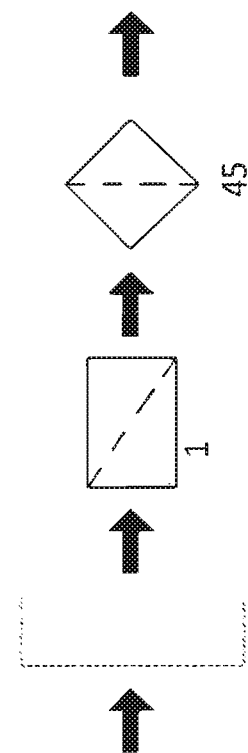

The embodiment, shown in FIG. 5C, comprises a crossflow diafiltration unit (1) of the invention before a final filtration step (45).

The process steps, shown in FIGS. 5A to 5C, can be expanded, as desired, to include additional process steps or can be combined, as desired. In this context the crossflow filtration of the invention is used preferably for filtration, diafiltration, concentration and/or modification of the composition of a solution.

LIST OF REFERENCE NUMERALS 1 crossflow diafiltration unit/diafiltration cassette
2 permeate
3 diafiltration medium
4 first filter material
5 feed fluid
6 second filter material
7 retentate 8 spacer
10 channel for reversing the feed fluid
11 standard crossflow cassette
12 diafiltration pump
14 feed fluid pump
16 manometer
17 throttle valve
19 conductometer
20 collection line
30a reservoir
30b reservoir
41 bioreactor
42 cell separation
44 chromatography
45 filtration step/filter

The invention claimed is:

1. A method for diafiltration of a feed fluid for obtaining a retentate and a permeate comprising:
(A) providing a crossflow filtration unit comprising a plurality of stacked arrays forming a filter cassette, wherein each of the arrays comprises, in sequence:
a diafiltration channel,
a flat first filter material,
a retentate channel,
a flat second filter material,
a permeate collection channel,
a further flat second filter material,
a further retentate channel, and
a further flat first filter material,
wherein:
the flat first filter material and the flat second filter material have respective pore sizes or respective molecular weight cut-offs;
each of the arrays of the crossflow filtration unit is arranged such that the flat first filter material delimits the diafiltration channel and the retentate channel from one another, the retentate channel is bounded by the flat first filter material and the flat second filter material, the flat second filter material delimits the retentate channel and the permeate collection channel from one another, the permeate collection channel is bounded by the flat second filter material and the further flat second filter material, the further flat second filter material delimits the permeate collection channel and the further retentate channel from one another, and the further retentate channel is bounded by the further flat second filter material and the further flat first filter material;
the diafiltration channel is connected to at least one inlet for conducting a diafiltration medium at a volume flow rate $V_{DF}$;
the retentate channel is connected to at least one inlet for conducting the feed fluid at a volume flow rate $V_{feed}$ and to at least one outlet for discharging the retentate at a volume flow rate $V_{retentate}$;
the permeate collection channel is connected in a fluid conducting manner to at least one outlet for the permeate,
(B) feeding the diafiltration medium into the at least one inlet for the diafiltration medium at the volume flow rate $V_{DF}$ and at a pressure $P_{DF}$;
(C) feeding the feed fluid into the at least one inlet for the feed fluid at the volume flow rate $V_{feed}$;
(D) discharging the retentate from the at least one outlet for the retentate at the volume flow rate $V_{retentate}$ and at a retentate outlet pressure $P_{retentate}$; and
(E) discharging the permeate from the at least one outlet for the permeate,
wherein said steps (B)-(E) are performed under conditions constrained as follows:

$$P_{DF} \geq P_{retentate};$$

$$V_{DF}/V_{feed} \geq 1; \text{ and}$$

$$V_{feed}/V_{retentate} \geq 1,$$

and wherein:
the diafiltration medium passes from the diafiltration channel into the retentate channel through the flat first filter material to obtain the retentate; and
the feed fluid enters the permeate collection channel through the flat second filter material to obtain the permeate.

2. The method for diafiltration, as claimed in claim 1, wherein the diafiltration medium and the feed fluid are fed continuously to the crossflow filtration unit.

3. The method for diafiltration, as claimed in claim 1, wherein:
crossflow filtration unit further comprises a plurality of the crossflow filtration units, each connected in series such that the at least one outlet for the retentate of a respective upstream crossflow filtration unit is connected in a fluid conducting manner to the at least one inlet for the feed fluid of a respective downstream crossflow filtration unit,
the feed fluid is fed into the at least one inlet for the feed fluid of the upstream crossflow filtration unit, that is not preceded by any other crossflow filtration unit, and
the retentate is discharged from the at least one outlet for the retentate of the downstream crossflow filtration unit, that is not followed by any other crossflow filtration unit.

4. The method for diafiltration, as claimed in claim 1, wherein the retentate, during discharging the retentate, is recycled at least partially into the at least one inlet for the feed fluid.

5. The method for diafiltration, as claimed in claim 1, further comprising:
separating a fluid into a pre-retentate and a pre-permeate, wherein the feed fluid comprises the pre-retentate or the pre-permeate.

6. The method for diafiltration, as claimed in claim 1, wherein the feed comprises a protein solution having an ion composition, and
wherein the ion composition of the protein solution is concentrated and/or modified with the crossflow filtration unit.

7. The method for diafiltration, as claimed in claim 1, further comprising performing continuous diafiltration within a chemical or biological process, wherein the continuous diafiltration is preceded by at least one conditioning step for the feed fluid and/or is followed by at least one post-conditioning step for the retentate.

8. The method for diafiltration, as claimed in claim 1, wherein the flat first filter material is a first filtration membrane; and/or the flat second filter material is a second filtration membrane.

9. The method for diafiltration, as claimed in claim 8, wherein the first filtration membrane is a microfiltration membrane or an ultrafiltration membrane, and/or the second filtration membrane is an ultrafiltration membrane.

10. The method for diafiltration, as claimed in claim 1, wherein a free volume of the diafiltration channel and/or the retentate channel decreases in a flow direction from the at least one inlet for the feed fluid to the at least one outlet for the retentate.

11. The method for diafiltration, as claimed in claim 10, wherein a plurality of layers of textile materials are arranged one above another in the retentate channel such that the free volume of the retentate channel decreases in the flow direction.

12. The method for diafiltration, as claimed in claim 1, wherein the pore size or the molecular weight cut-off of the flat first filter material is at least as large as the pore size or the molecular weight cut-off of the flat second filter material.

13. The method for diafiltration as claimed in claim 1, wherein the conditions are further constrained as follows:

$$3 \le V_{DF}/V_{feed} \le 10.$$

14. The method for diafiltration, as claimed in claim 1, wherein:
during said step (B), the diafiltration medium passes from the diafiltration channel into the retentate channel exclusively through the flat first filter material.

15. The method for diafiltration, as claimed in claim 14, wherein the feed fluid and the diafiltration medium enter the permeate collection channel exclusively through the flat second filter material.

16. The method for diafiltration, as claimed in claim 1, wherein:
at least during said steps (B)-(E), the feed fluid and the diafiltration medium enter the permeate collection channel exclusively through the flat second filter material and exit the permeate collection channel exclusively through the at least one outlet for the permeate;
during said step (B), the diafiltration medium passes from the diafiltration channel into the retentate channel exclusively through the flat first filter material; and
during said step (C), the feed fluid passes into the retentate channel through the at least one inlet for the feed fluid, and passes from the retentate channel into the permeate collection channel exclusively through the flat second filter material.

17. The method for diafiltration, as claimed in claim 16, wherein the diafiltration medium and the feed fluid are fed continuously to the crossflow filtration unit at least during said steps (B) and (C).

18. The method for diafiltration, as claimed in claim 1, wherein:
the feed fluid and the diafiltration medium enter the permeate collection channel exclusively through the flat second filter material and exit the permeate collection channel exclusively through the at least one outlet for the permeate,
during said step (B), the diafiltration medium enters into the at least one inlet for the diafiltration medium at the volume flow rate $V_{DF}$ and at the pressure $P_{DF}$;
wherein said steps (B) and (C) are performed continuously, and
wherein said method for diafiltration further comprises:
(F) conveying the diafiltration medium in the retentate channel and the feed fluid in the retentate channel either through the flat second filter material or to the at least one outlet for discharging the retentate.

19. The method for diafiltration, as claimed in claim 18, wherein, at least during said steps (B)-(F), the diafiltration medium enters the diafiltration channel through the at least one inlet for conducting the diafiltration medium and exits the diafiltration channel exclusively through the flat first filter material, and
wherein, at least during said steps (B)-(F), the feed fluid and the diafiltration medium enter the permeate collection channel exclusively through the flat second filter material and exit the permeate collection channel exclusively through the at least one outlet for the permeate.

20. The method for diafiltration, as claimed in claim 18, wherein the diafiltration medium and the feed fluid are fed continuously to the crossflow filtration unit at least during said steps (B), (C) and (F).

21. The method for diafiltration, as claimed in claim 1, wherein the diafiltration channel, the retentate channel, the permeate collection channel, and the further retentate channel collectively form a plurality of channels feeding the diafiltration medium, the feed fluid, or the permeate, and wherein each of the plurality of channels comprises respective spacers configured and arranged to hold open the plurality of channels for the diafiltration medium, the feed fluid, or the permeate.

* * * * *